US012329754B2

(12) United States Patent
Cen et al.

(10) Patent No.: US 12,329,754 B2
(45) Date of Patent: *Jun. 17, 2025

(54) USE OF BERBAMINE DIHYDROCHLORIDE IN PREPARATION OF EBOLA VIRUS INHIBITOR

(71) Applicant: Institute of Medicinal Biotechnology, Chinese Academy of Medical Sciences, Beijing (CN)

(72) Inventors: Shan Cen, Beijing (CN); Quanjie Li, Beijing (CN); Dongrong Yi, Beijing (CN); Yi Shi, Beijing (CN); Han Wang, Beijing (CN); Jinming Zhou, Beijing (CN)

(73) Assignee: Institute of Medicinal Biotechnology, Chinese Academy of Medical Sciences, Beijing (CN)

( * ) Notice: Subject to any disclaimer, the term of this patent is extended or adjusted under 35 U.S.C. 154(b) by 318 days.

This patent is subject to a terminal disclaimer.

(21) Appl. No.: 18/132,530

(22) Filed: Apr. 10, 2023

(65) Prior Publication Data

US 2023/0321079 A1   Oct. 12, 2023

Related U.S. Application Data

(62) Division of application No. 16/652,372, filed as application No. PCT/CN2019/091838 on Jun. 19, 2019, now Pat. No. 11,654,141.

(30) Foreign Application Priority Data

Aug. 1, 2018   (CN) .......................... 201810863809.5

(51) Int. Cl.
   *A61K 31/472*   (2006.01)
   *A61P 31/14*   (2006.01)

(52) U.S. Cl.
   CPC ............ *A61K 31/472* (2013.01); *A61P 31/14* (2018.01)

(58) Field of Classification Search
   None
   See application file for complete search history.

(56) References Cited

U.S. PATENT DOCUMENTS

2014/0275139 A1*   9/2014   Van Dyke .......... A61K 31/4745
                                            514/279
2022/0257588 A1    8/2022   Yue et al.

FOREIGN PATENT DOCUMENTS

| CN | 101273989 A | 10/2008 |
| CN | 101429201 A | 5/2009 |
| CN | 103059017 A | 4/2013 |
| CN | 109125323 A | 1/2019 |

OTHER PUBLICATIONS

Onai et al. Planta Med. 1995, 61, 497-501. (Year: 1995).*
Zhang et al. Advances in Clinical Medicine 2015, 5, 136-165. Machine translation. (Year: 2015).*
Zhang, Ying; Hu, Wenxiang. "Progress in Research of Activity of Anti-Ebola Virus and Effect of Pharmacology of Tetrandrine." Advances in Clinical Medicine, 2015, 5(3), 136-165. Hans. Web. http://www.hanspub.org/journal/acm/.
International Search Report (Chinese w/ English Translation) for PCT/CN2019/091838 dated Sep. 19, 2019.; ISA/CN.
Brunhofer et al. Exploration of natural compounds as sources of new bifunctional scaffolds targeting cholinesterases and beta amyloid aggregation: The case of chelerythrine'1 Bioorg. Med. Chem. Lett. 2012, 20, 6669-6679. (Year: 2012).
NIH National Library of Medicine, PubChem Database [online] CID 16217067, created Jul. 16, 2007. (Year: 2007).

* cited by examiner

*Primary Examiner* — Amanda L. Aguirre
(74) *Attorney, Agent, or Firm* — Harness, Dickey & Pierce, P.L.C.

(57)   ABSTRACT

The present invention provides use of berbamine dihydrochloride in preparation of an Ebola virus inhibitor. In the present invention, the primed glycoprotein of the Ebola virus (EBOV-GPcl) is taken as a target site, and an antiviral active compound with the capability of binding to the EBOV-GPcl, i.e., berbamine dihydrochloride, is obtained through structure-based virtual screening. Berbamine dihydrochloride can specifically inhibit the entry of an Ebola recombinant virus by binding to the target protein EBOV-GPcl, thereby achieving the effect of anti-Ebola virus infection. The half-maximum effect concentration (EC50) of berbamine dihydrochloride against EBOV is 0.49 μM, which indicates that berbamine dihydrochloride has a strong inhibition effect on EBOV.

4 Claims, 4 Drawing Sheets

FIG. 1

Prior art

FIG. 2

USE OF BERBAMINE DIHYDROCHLORIDE IN PREPARATION OF EBOLA VIRUS INHIBITOR

CROSS-REFERENCE TO RELATED APPLICATIONS

This application is a divisional of U.S. application Ser. No. 16/652,372, filed Mar. 3, 2020 which is a National Phase of PCT/CN2019/091838 filed Jun. 19, 2019, which claims priority to and the benefit of Chinese patent application No. 201810863809.5 filed to the National Intellectual Property Administration on Aug. 1, 2018 and entitled "USE OF BERBAMINE DIHYDROCHLORIDE IN PREPARATION OF EBOLA VIRUS INHIBITOR", the entire disclosures of the above applications are incorporated herein by reference.

TECHNICAL FIELD

The present application relates to use of berbamine dihydrochloride, and in particular to use of berbamine dihydrochloride in preparation of an Ebola virus inhibitor.

BACKGROUND

A viral hemorrhagic fever is a group of natural focus diseases that are caused by viruses and characterized by fever, hemorrhage and shock as main clinical features. Such diseases are widely distributed in the world, with more serious clinical manifestations and high mortality. At present, more than ten kinds of such diseases have been found in the world. The common viral hemorrhagic fever includes Ebola hemorrhagic fever, Marburg hemorrhagic fever, Lassa fever, Crimean-Congo hemorrhagic fever, Rift Valley fever, dengue hemorrhagic fever, yellow fever and smallpox, etc.

The Ebola hemorrhagic fever (Ebola virus disease) is an acute hemorrhagic infectious disease caused by an Ebola virus (EBOV) of filoviridae, which has a mortality rate up to 90% and is one of the most deadly viral infectious diseases in human beings. EBOV can be divided into five species: a Zaire ebolavirus (ZEBOV), a Sudanebolavirus (SUDV), a Tai Forest ebolavirus (TAFV), a Bundibugyoebolavirus (BDBV), and a Reston ebolavirus (RESTV). Among them, the ZEBOV has the strongest pathogenicity.

The Marburg haemorrhagic fever is an acute febrile disease that is caused by a Marberg virus (MARV) and has severe hemorrhage. It belongs to the same family as the Ebola hemorrhagic fever, both of them are highly lethal infectious diseases. The Marburg virus and the Ebola virus belong to the genus Filovirus of Filoviridae.

The Lassa fever is an acute infectious disease that is caused by a Lassa virus (LASV) and mainly transmitted by rodents. The Lassa virus belongs to the genus Mammarenavirus of Arenaviridae.

An envelope glycoprotein (GP) refers to a glycoprotein encoded by a virus itself and coated on an outer layer of the virus. The GP is a multifunctional protein, which plays a vital role in processes of adsorption and penetration of a virus into a host cell, pathogenicity of the virus, down-regulation of protein expression on the surface of the host cell by the virus, and increase of virus assembly and budding.

At present, symptomatic and supportive treatments are mainly adopted for the viral hemorrhagic fever, and there are no specific therapeutic drugs and vaccines that have been systematically clinically verified to be effective.

SUMMARY

The technical problem to be solved by the present invention is how to inhibit viruses causing a viral hemorrhagic fever, such as an Ebola virus, a Marburg virus and/or a Lassa virus.

In order to solve the above technical problems, the present invention provides use of berbamine dihydrochloride.

Berbamine dihydrochloride has a structural formula shown in FIG. 1, and its CAS accession number is 6078-17-7.

The use of berbamine dihydrochloride provided by the present invention is any one of U1 to U5:

U1. use of berbamine dihydrochloride or a pharmaceutically acceptable salt thereof in preparation of a virus inhibitor; where the virus is capable of binding to berbamine dihydrochloride or a pharmaceutically acceptable salt thereof through a primed glycoprotein;

U2. use of berbamine dihydrochloride or a pharmaceutically acceptable salt thereof in inhibiting a virus; where the virus is capable of binding to berbamine dihydrochloride or a pharmaceutically acceptable salt thereof through a primed glycoprotein;

U3. use of berbamine dihydrochloride or a pharmaceutically acceptable salt thereof in preparation of a product (such as a drug, a vaccine or a pharmaceutical preparation) for treating and/or preventing a viral hemorrhagic fever; where the viral hemorrhagic fever may be a disease caused by a virus capable of binding to berbamine dihydrochloride or a pharmaceutically acceptable salt thereof through a primed glycoprotein;

U4. use of berbamine dihydrochloride or a pharmaceutically acceptable salt thereof in the treatment and/or prevention of a viral hemorrhagic fever; where the viral hemorrhagic fever may be a disease caused by a virus capable of binding to berbamine dihydrochloride or a pharmaceutically acceptable salt thereof through a primed glycoprotein; and U5. use of berbamine dihydrochloride or a pharmaceutically acceptable salt thereof in preparation of a product (such as a drug, a vaccine or a pharmaceutical preparation) that binds to a primed viral glycoprotein.

In the above uses, the virus may be a virus of Filoviridae and/or Arenaviridae, such as a virus causing the viral hemorrhagic fever. The virus causing the viral hemorrhagic fever may be an Ebola virus, a Marburg virus and/or a Lassa virus.

In the above uses, the viral hemorrhagic fever may be an Ebola hemorrhagic fever, a Marburg hemorrhagic fever and/or a Lassa fever.

In the above uses, in addition to berbamine dihydrochloride or a pharmaceutically acceptable salt thereof, the virus inhibitor, the product for treating and/or preventing the viral hemorrhagic fever and the product binding to the primed viral glycoprotein may also contain an appropriate carrier or excipient. Herein the carrier material includes, but are not limited to, a water-soluble carrier material (such as polyethylene glycol, polyvinylpyrrolidone, an organic acid, etc.), an insoluble carrier material (such as ethyl cellulose, cholesterol stearate, etc.), and an enteric carrier material (such as cellulose acetate phthalate, carboxymethylcellulose, etc.). Among them, the water-soluble carrier material is preferred. By using these materials, various dosage forms can be made, including but not limited to a tablet, a capsule, a dropping pill, an aerosol, a pellet, powder, a solution, a suspension, an emulsion, a granule, a liposome, a transdermal agent, a buccal tablet, a suppository, lyophilized powder for injection, etc. The dosage form can be a common preparation, a sustained-release preparation, a controlled-release preparation, and various microparticle administration systems. Various carriers well known in the art can be widely used in order to prepare a unit dosage form into a tablet. Examples of the carriers are, for example, a diluent and an absorbent, such as starch, dextrin, calcium sulfate, lactose, mannitol, sucrose, sodium chloride, glucose, urea, calcium carbonate, porcellanite, microcrystalline cellulose, aluminum silicate, and the like; a humectant and a binder, such as water, glycerol, polyethylene glycol, ethanol, propanol, starch slurry, dextrin, syrup, honey, glucose solution, *Mucilago acaciae*, gelatin slurry, sodium carboxymethylcellulose, lac, methylcellulose, potassium phosphate, polyvinylpyrrolidone, and the like; a disintegrating agent, such as dried starch, alginate, agar powder, laminaran, sodium bicarbonate and citric acid, calcium carbonate, polyoxyethylene, sorbitol fatty acid ester, sodium dodecyl sulfate, methyl cellulose, ethyl cellulose, and the like; a disintegration inhibitor, such as sucrose, glyceryl tristearate, cocoa butter, hydrogenated oil, and the like; an absorption promoter, such as a quaternary ammonium salt, sodium dodecyl sulfate, and the like; and a lubricant, such as talc, silica, corn starch, stearate, boric acid, liquid paraffin, polyethylene glycol, and the like. The tablet can also be further made into a coated tablet, such as a sugar-coated tablet, a film-coated tablet, an enteric coated tablet, or a double-layer tablet and a multi-layer tablet. Various carriers well known in the art can be widely used in order to prepare a unit dosage form into a pellet. Examples of the carriers are, for example, a diluent and an absorbent, such as glucose, lactose, starch, cocoa butter, hydrogenated vegetable oil, polyvinylpyrrolidone, Gelucire, kaolin, talc, and the like; a binder, such as Arabic gum, tragacanth gum, gelatin, ethanol, honey, liquid sugar, rice paste or panada, and the like; a disintegrating agent, such as agar powder, dried starch, alginate, sodium dodecyl sulfate, methyl cellulose, ethyl cellulose, and the like. Various carriers well known in the art can be widely used in order to prepare a unit dosage form into a suppository. Examples of the carriers are, for example, polyethylene glycol, lecithin, cocoa butter, higher alcohols, esters of higher alcohols, gelatin, semisynthetic glycerides, and the like. In order to prepare an unit dosage form into an injection preparation, such as a solution, an emulsion, lyophilized powder for injection and a suspension, all diluents commonly used in the art can be used, for example, water, ethanol, polyethylene glycol, 1,3-propanediol, ethoxylated isostearyl alcohol, polyoxidized isostearyl alcohol, polyoxyethylene sorbitan fatty acid ester, and the like. Furthermore, in order to prepare an isotonic injection, an appropriate amount of sodium chloride, glucose or glycerin can be added into the injection preparation, and moreover, a conventional cosolvent, a conventional buffer, a conventional pH regulator, and the like may also be added. Furthermore, a colorant, a preservative, a perfume, a flavoring agent, a sweetener or other materials can also be added into the pharmaceutical preparation if desired. The above dosage forms can be administered by injection, including subcutaneous injection, intravenous injection, intramuscular injection and intracavitary injection, etc.; cavitary mucosal drug delivery, such as transrectal and vaginal administration; pulmonary administration, such as nasal administration; and mucosal administration.

The present invention also provides a pharmaceutical compound.

The pharmaceutical compound provided by the present invention is berbamine dihydrochloride or a pharmaceutically acceptable salt thereof.

Among the above pharmaceutical compounds, the pharmaceutical compound can be used for inhibiting a virus from infecting an animal. The virus is capable of binding to berbamine dihydrochloride or a pharmaceutically acceptable salt thereof through a primed glycoprotein. The virus may be a virus of Filoviridae and/or Arenaviridae, such as a virus causing the viral hemorrhagic fever. The virus causing the viral hemorrhagic fever may be an Ebola virus, a Marburg virus and/or a Lassa virus.

The invention also provides a method for inhibiting a virus from infecting an animal.

The method for inhibiting a virus from infecting an animal as provided by the present invention includes: administering berbamine dihydrochloride or a pharmaceutically acceptable salt thereof to a recipient animal to inhibit the virus from infecting the animal; where the virus is capable of binding to berbamine dihydrochloride or a pharmaceutically acceptable salt thereof through a primed glycoprotein. Furthermore, the virus may be a virus of Filoviridae and/or Arenaviridae, such as a virus causing the viral hemorrhagic fever. The virus causing the viral hemorrhagic fever may be an Ebola virus, a Marburg virus and/or a Lassa virus.

The present invention also provides a method for treating and/or preventing a viral hemorrhagic fever.

The method for treating and/or preventing a viral hemorrhagic fever as provided by the present invention includes: administering berbamine dihydrochloride or a pharmaceutically acceptable salt thereof to a recipient animal to treat and/or prevent the viral hemorrhagic fever; where the viral hemorrhagic fever may be a disease caused by a virus capable of binding to berbamine dihydrochloride or a pharmaceutically acceptable salt thereof through a primed glycoprotein.

In the present invention, the animal may be a mammal, such as human beings; and the animal can also be other animals infected by the virus other than mammals, such as poultry.

In the present invention, the term "a pharmaceutically acceptable salt" refers to a salt that is suitable for in contact with tissues of human beings and lower animals without excessive toxicity, irritation, allergic reactions, etc. within a reliable range of medical judgment, and is commensurate with a reasonable effect/risk ratio. The pharmaceutically acceptable salt is well known in the art. For example, the pharmaceutically acceptable salt is described in detail in M. Berge, et al., J. Pharmaceutical Sciences, 1977, 66:1.

In the present invention, the Ebola virus may be a Zaire ebolavirus (ZEBOV), a Sudanebolavirus (SUDV), a Tai Forest ebolavirus (TAFV), a Bundibugyoebolavirus (BDBV), and/or a Reston ebolavirus (RESTV).

In the present invention, the inhibition of the virus may also be referred to as anti-virus. The inhibition of the virus can be inhibiting the virus from invading a cell. The inhibiting the virus from invading a cell may be inhibiting a virus from entering into the cell as mediated by a primed viral glycoprotein (GPcl).

In the present invention, the primed glycoprotein of the Ebola virus (EBOV-GPcl) is taken as a target site, and an antiviral active compound with the capability of binding to the EBOV-GPcl, i.e., berbamine dihydrochloride, is obtained through structure-based virtual screening. Berbamine dihydrochloride can specifically inhibit the entry of an Ebola recombinant virus by binding to the target protein EBOV-GPcl, thereby achieving the effect of anti-Ebola virus infection. The half-maximum effect concentration (EC50) of berbamine dihydrochloride against EBOV is 0.49 μM, which indicates that berbamine dihydrochloride has a strong inhibition effect on EBOV

BRIEF DESCRIPTION OF THE DRAWING

FIG. 1 shows a structural formula of berbamine dihydrochloride.

FIG. 2 shows that berbamine dihydrochloride in embodiment 1 has a specific inhibition effect on the entry of a EBOV-Zaire GP/HIV-luc recombinant virus; in FIG. 2, VSVG represents VSV-G/HIV-luc, Ebola-GP represents EBOV-Zaire GP/HIV-luc, a virus infection rate=1–an inhibition rate, DMSO represents blank control treatment, TET represents a treatment with tetrandrine, 1-22 represent 22 treatments with compounds respectively, where 10 of them are treatments with berbamine dihydrochloride.

DETAILED DESCRIPTION

Figure 3:
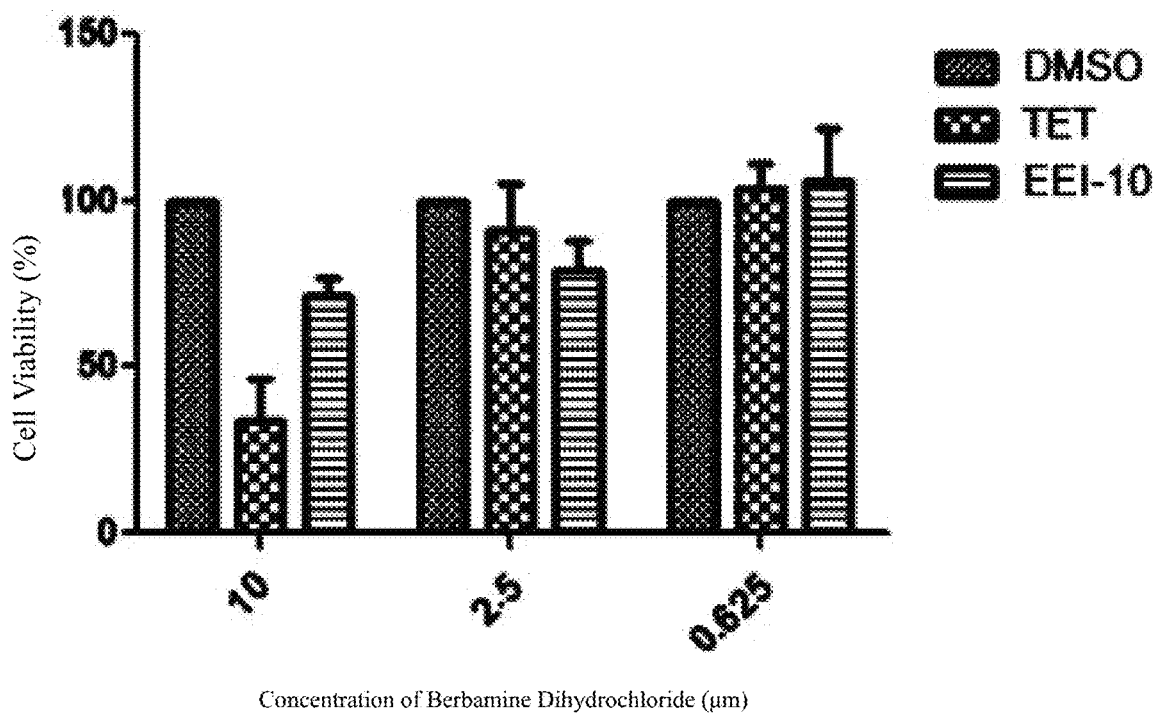
FIG. 3 shows that a cell growth experiment in embodiment 2 verifies the effect of berbamine dihydrochloride on the growth of a 293T cell; and in FIG. 3, DMSO represents blank control treatment, TET represents a treatment with tetrandrine, and EEI-10 represents a treatment with berbamine dihydrochloride.

The present invention will be described in further detail below with reference to specific embodiments. The embodiments given are only for the purpose of illustrating the present invention, and are not intended to limit the scope of the present invention. The embodiments provided below can serve as a guide for further improvement by those of ordinary skills in the art, and are not intended to limit the present invention in any way.

Unless otherwise specified, the experimental methods in the following embodiments are conventional methods well known to those skilled in the art or according to the conditions suggested by a manufacturer. The materials, reagents, etc. used in the following embodiments are all commercially available, unless otherwise specified.

Berbamine dihydrochloride is a known commercially-available compound. A specific acquisition means of it is the prior art. The present invention is not particularly limited to this. Berbamine dihydrochloride in the following embodiments is a product available from TargetMol.

A eukaryotic expression vector pcDNA3.1(+) in the following embodiments is a product available from Invitrogen.

In the following embodiments, the biomaterial, a HIV-luc plasmid pNL4-3Luc(R-E-) carrying a luciferase reporter gene (Ma, L., et al. (23 May 2018). "Identification of small molecule compounds targeting the interaction of HIV-1Vif and human APOBEC3G by virtual screening and biological evaluation." Sci Rep 8(1):8067), is available to the public from the Institute of Medical Biotechnology, Chinese Academy of Medical Sciences. The biomaterial is only used for repeating the experiment of the present invention, and cannot be used for other purposes.

Studies of predecessors have shown that the glycoprotein of an Ebola virus (EBOV-GP) undergoes enzymatic cleavage after entering a lysosome, and the primed glycoprotein (Primed GP, GPcl) after the enzymatic cleavage can directly interact with an endocytosis receptor-human cholesterol transfer protein (Niemann-Pick C1, NPC1), thereby initiating a membrane fusion process between the virus and a host cell. In the present invention, according to the interaction between EBOV-GPcl (the primed glycoprotein of the Ebola virus) and NPC1-C, by adopting a brand-new drug design method, the inventor designs and synthesizes an active polypeptide which specifically binds to the EBOV-GPcl and can inhibit the Ebola virus from entering a cell. According to a hydrogen bond, electrostatic interaction and hydrophobic interaction, and the like between the active polypeptide and the EBOV-GPcl, the inventor constructs a pharmacophore model, and establishes a virtual screening method for EBOV-GPcl-targeting inhibitors for inhibition the entry of the Ebola virus, in order to find a small-molecular compound that specifically binds to the EBOV-GPcl, thereby inhibiting the binding of the EBOV-GPcl to NPC1-C and further inhibiting the replication of the Ebola virus. A database is screened by using this model, and a target compound is finally obtained through scoring by multiple software. The target compound is detected for a biological activity, and finally an antiviral active compound with the EBOV-GPcl as a target site is obtained. The compound is berbamine dihydrochloride, which has the capacity of binding to EBOV-GPcl.

EBOV is listed as a virus with a dangerousness of level 4, so that the present invention uses a pseudovirus technology, which is a safe and effective research means, to evaluate the biological activity of the small-molecule compound at an in vitro level. A replication-defective pseudovirus EBOV-GP/HIV-luc is prepared by encapsulating an HIV core with the GP protein of the most toxic Zaire EBOV, and the antiviral activity of the sample is judged by a fluorescence reporter gene detection technology. Meanwhile, a VSVG/HIV-luc recombinant virus model is used for analyzing the specificity of small molecule compounds. After cytotoxicity is eliminated, the action mechanism of the small-molecule compound is further verified by a drug TOA (Time of addition) experiment. Finally, the capability of the small-molecule compound of binding to the target protein GPcl is determined in vitro by using the BioLayer Interferometry technology based on an optical fiber biosensor, so as to verify the targeting property of the small-molecule compound. The specific experimental methods and results are as follows:

Embodiment 1. Verification of Berbamine Dihydrochloride being Capable of Specifically Inhibit the Activity of EBOV by Using a Screening Model for an EBOV Entry Inhibitor By using a cell-level recombinant virus technology, A GP of a Zaire-EBOV was co-expressed with an HIV core plasmid (pNL4-3.Luc) to prepare a recombinant virus, and the antiviral activity of a compound was evaluated using a high-throughput screening model of a GP-protein-targeting EBOV entry inhibitor. The specific steps were as follows.

293T cells were taken and cultured. When the cells were grown to confluence in the culture bottle, the old culture medium was discarded, and the cells were digested with a digestive juice containing 0.25% pancreatin and 0.02% EDTA. When the cells became round, the digestive juice was discarded, the cells were immediately added with a high-sugar DMEM medium (GIBICO) containing 10% FBS (purchased from GIBCO), and gently pipetted up and down at the bottom of the bottle with a pipette to completely separate the cells from the bottom of the bottle and disperse them into a single-cell suspension. After counting, the cell concentration was adjusted to 2.2×105 cells/ml with the culture medium, and the cells were inoculated into a 6-well plate at 2 mL/well. After 24 hours (with a cell abundance of about 70%), transfection was carried out with plasmids at the dosage of: 2 μg of pZEBOV-GP and 3 μg of a HIV-luc plasmid pNL4-3Luc(R-E-) carrying a luciferase reporter gene, by using a transfection reagent of Lipofectamine 2000 (Invitrogen), according to the operation instruction, so as to generate an Ebola pseudotype virus, which was named EBOV-Zaire GP/HIV-luc. The Supernatant containing the pseudotype virus was collected 48 hours after the transfection, combined, clarified from floating cells and cell debris by low speed centrifugation, and filtered through a filter with a pore size of 0.45 μm. Pseudovirus particles were quantified by measuring the level of virus-related HIV p24 using a ELISA assay.

pZEBOV-GP was a recombinant expression plasmid expressing the glycoprotein (GP) of Zaire-EBOV, that was obtained by inserting positions 5900-8305 of the GP gene (GenBank Accession No. KJ660347.2) (Update Date Dec. 18, 2014 01:25 PM) of Zaire ebolavirus isolate *H. sapiens-wt*/GIN/2014/Makona-Gueckedou-C07 into a vector pcDNA3.1(+).

The EBOV-Zaire GP/HIV-luc pseudovirus particles were incubated together with the 293T cells into a 96-well plate. After 48 hours, cells were collected and lysed to measure the activity of a firefly luciferase. The value of the luciferase activity represented viral infection.

The compounds were dissolved in DMSO, then respectively mixed with the EBOV-Zaire GP/HIV-luc pseudovirus, and added into the 293T cells, so that the compound content was 10 μm. After 48 hours, the 293T cells were lysed, and the viral inhibition rates of the compounds were evaluated by measuring a luciferase activity. The solvent DMSO was used as a blank control, and meanwhile the EBOV entry inhibitor, tetrandrine (TET), was introduced as a control. Tetrandrine was dissolved in DMSO, then mixed with the EBOV-Zaire GP/HIV-luc pseudovirus, and added into the 293T cells, so that the tetrandrine content was 1 μm. After 48 hours, the 293T cells were lysed, and the viral inhibition rates of the compounds were evaluated by measuring a luciferase activity. The viral inhibition rate of the compound=1−relative luciferase activity. The relative luciferase activity referred to the luciferase activity relative to the blank control. The luciferase activity actually represented viral infectivity.

Figures 1, 2:
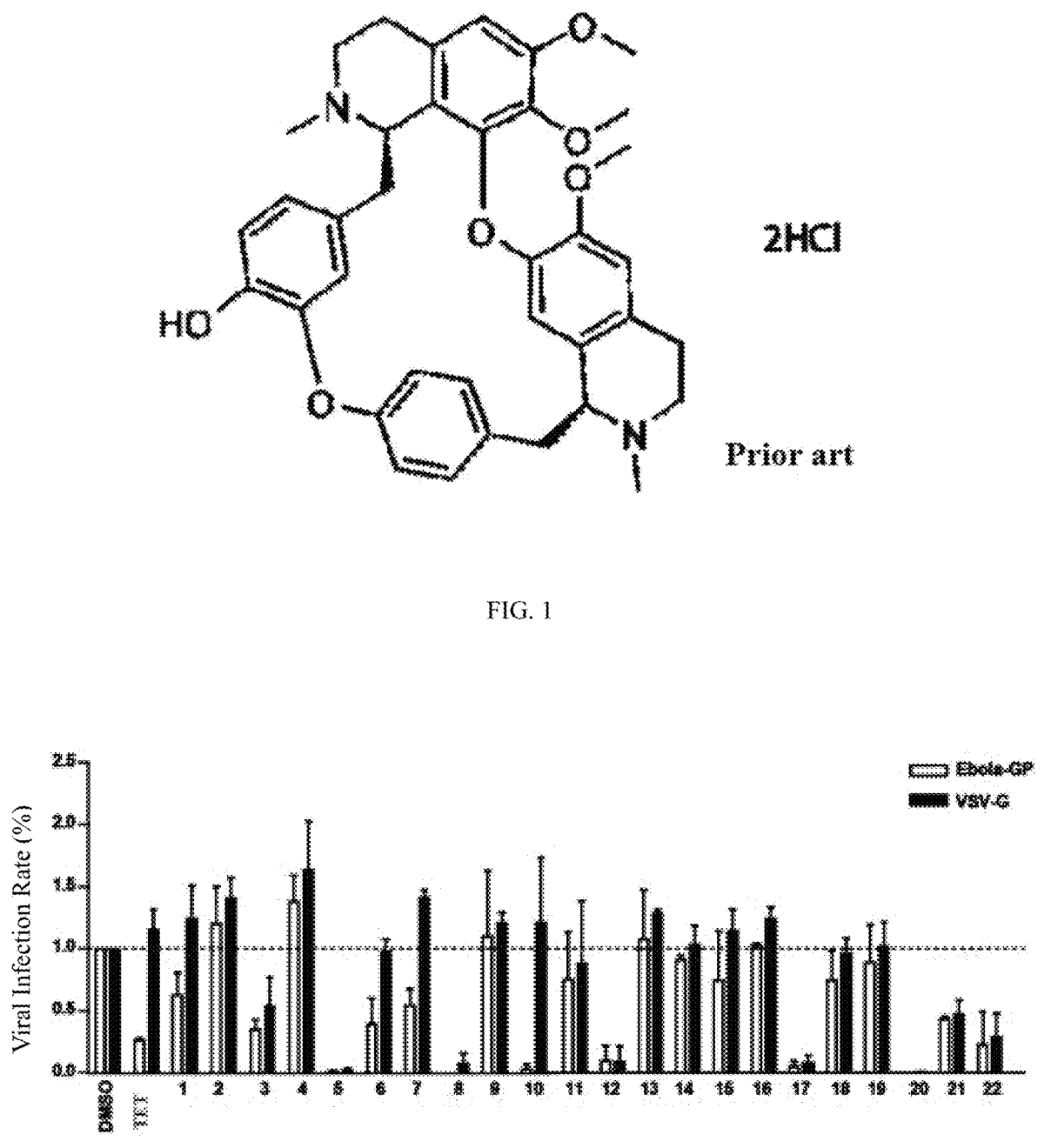

Most EBOV inhibitors currently known were broad-spectrum antiviral drugs. In order to find narrow-spectrum inhibitors for EBOV, the specificity analysis of the screened active compounds was required. Because vesicular stomatitis virus glycoprotein (VSVG) had similar functions as EBOV-GPcl and played an important role in the recognition of viruses and receptors, the compound was subjected to specificity analysis by using the VSVG-expressing pseudovirus VSV-G/HIV-luc. After cytotoxic factors were eliminated, the inhibitory activity of the compound on the VSV-G/HIV-luc pseudovirus was also detected with the same method as above, by using the luciferase principle. If the compound only had an obvious inhibition effect on EBOV-GPcl-mediated virus entry, but had no or very low inhibition rate on VSV, then the compound had specificity for EBOV The experiment was conducted in triplicate, and the results were shown in FIG. 2. The compound berbamine dihydrochloride had an inhibition rate over 80% on the EBOV-Zaire GP/HIV-luc pseudovirus, and had almost no inhibition effect on the VSV-G/HIV-luc pseudovirus at the same concentration. This showed that berbamine dihydrochloride had a specific inhibition effect on the EBOV-Zaire GP/HIV-luc pseudovirus. As a positive control, the EBOV entry inhibitor, tetrandrine (TET) had a selective inhibition effect similar to that of berbamine dihydrochloride.

The preparation method of the VSV-GP-expressing pseudovirus VSV-G/HIV-luc differs from that of the EBOV-Zaire GP/HIV-luc only in that pZEBOV-GP in the preparation method of the EBOV-Zaire GP/HIV-luc was replaced by pVSV-GP, with other operations being exactly the same. PVSV-GP was a VSVG-expressing recombinant expression plasmid obtained by inserting positions 14-1567 of the VSVG GP gene (GenBank Accession No. V01214.1) (Update Date Feb. 4, 2011) into the vector pcDNA3.1(+).

Embodiment 2: The Antiviral Activity of Berbamine Dihydrochloride Having Nothing to do with its Cytotoxicity In order to eliminate non-specificity differences caused by toxicity of compounds, a cellCounting Kit-8 (CCK-8) was used to evaluate the effect of berbamine dihydrochloride on the growth of the 293T cells.

CCK-8 kit was a kit for detecting cell proliferation, cell survival and cytotoxicity, and was a widely used, rapid, and highly-sensitive detection kit based on WST-8 (a water-soluble tetrazolium salt, with the chemical name of: 2-(2-methoxy-4-nitrophenyl)-3-(4-nitrophenyl)-5-(2,4-disulfobenzene)-2H-tetrazolium monosodium salt). It was an alternative to a MTT method. In the kit, the water-soluble tetrazolium salt-WST-8 was used, which can be reduced by some dehydrogenases in mitochondria to generate orange formazan in the presence of an electron coupling reagent. The cells proliferated in a larger number and faster had a darker color; and when the cytotoxicity was greater, the color was lighter. For the same cells, there was a good linear relationship between the depth of color and the number of cells. The light absorption value of the cell was determined through an enzyme-linked immunometric meter at a wavelength of 450 nm, which could indirectly reflect the number of living cells. The specific steps were as follows.

The 293T cells were cultured in a 96-well plate and incubated with berbamine dihydrochloride (dissolved in DMSO). The contents of berbamine dihydrochloride in the culture medium were 10 μM, 2.5 μM and 0.625 μM respectively. After 48 hours, the cell supernatant was replaced by a cell culture solution containing a 10% CCK-8 reagent, and the cells were continually cultured in a 5% CO2 incubator at 37° C. for 1 h. The optical density (OD) value of each well at 450 nm was recorded on a microplate reader (Thermo, Varioskan Flash).

Taking tetrandrine (TET) as a control, the 293T cells were cultured in a 96-well plate and incubated with tetrandrine (dissolved in DMSO). The contents of tetrandrine in the culture medium were 10 μM, 2.5 μM and 0.625 μM respectively. After 48 hours, the cell supernatant was replaced by a cell culture solution containing a 10% CCK-8 reagent, and the cells were continually cultured in a 5% CO2 incubator at 37° C. for 1 h. The optical density (OD) value of each well at 450 nm was recorded on a microplate reader (Thermo, Varioskan Flash).

The solvent DMSO was used as a blank control (DMSO). The OD450 nm of the blank control was recorded as cell viability of 100%.

The experiment was conducted in triplicate. Results were shown in FIG. 3, which indicated that, at the highest concentration of 10 µM (much higher than the measured IC50 value), berbamine dihydrochloride had no significant effect on cell activity. Thus it could be concluded that, the antiviral activity of berbamine dihydrochloride had nothing to do with its cytotoxicity.

Figure 4:
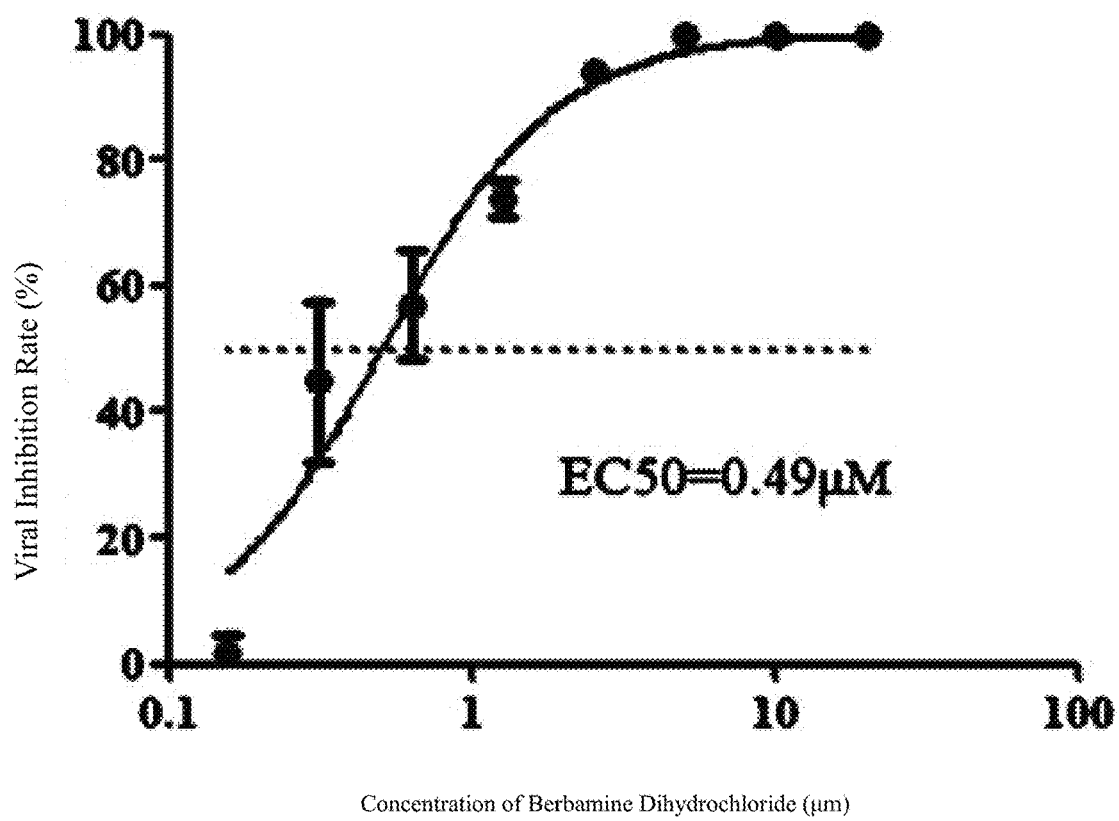
FIG. 4 shows that berbamine dihydrochloride has a good dose-dependent inhibition effect on the EBOV-Zaire GP/HIV-luc recombinant virus in embodiment 3.

Embodiment 3. Berbamine Dihydrochloride Having a Good Dose-Dependent Inhibition Effect on EBOV Referring to the method in Embodiment 1, berbamine dihydrochloride was dissolved in DMSO, then mixed with EBOV-Zaire GP/HIV-luc in Embodiment 1 respectively, and then added into the 293T cells to make the contents of berbamine dihydrochloride be 0.15625, 0.3125, 0.625, 1.25, 2.5, 5, 10 and 20 µM respectively. After 48 hours, the 293T cells were lysed, and the anti-EBOV activity of berbamine dihydrochloride was evaluated by measuring the luciferase activity. By using the solvent DMSO as a blank control (DMSO), the luciferase activity of the blank control was considered as the cell viability of 100%. The experiment was conducted in triplicate, and the results were shown in FIG. 4. Berbamine dihydrochloride significantly inhibited the activity of the EBOV-Zaire GP/HIV-luc pseudovirus in a dose-dependent manner. The half-maximum effect concentration (EC50) of berbamine dihydrochloride against EBOV was 0.49 µm.

Embodiment 4: Berbamine Dihydrochloride Acting on the Entering Stage of a Virus, as Determined by a Drug TOA Experiment The specific inhibitory action of berbamine dihydrochloride on the EBOV-Zaire GP/HIV-luc pseudovirus indicated that they may act as EBVO entry inhibitors. In order to verify this point, the acting phase of berbamine dihydrochloride in the virus infection cycle was studied through a drug TOA (Time of addition) experiment. The specific steps were as follows.

On the day before infection, the 293T cells were inoculated into a 96-well plate according to the cell number of 6×104 cells/well, and respectively added with 50 µL of the EBOV-Zaire GP/HIV-LUC of Embodiment 1. Before the infection (−1 hour), during the infection (0 hour) and at time points of 2, 4, 6, 8, 10, 12, 14 and 16 h after the infection, the cells were added with berbamine dihydrochloride (dissolved in DMSO, with the content (final concentration) in the medium of 1×10−5 mol·L−1), with the EBOV entry inhibitor tetrandrine (TET) (dissolved in DMSO, with the content in the medium of 1×10−7 mol·L−1), the non-nucleoside reverse transcriptase inhibitor efavirenz (EFV) (dissolved in DMSO, with the content in the medium of 1×10−9 mol·L−1) as controls, and DMSO as the solvent control. After 48 hours of infection, the luciferase activity of the reporter gene was detected to reflect the replication level of the recombinant virus.

Figure 5:
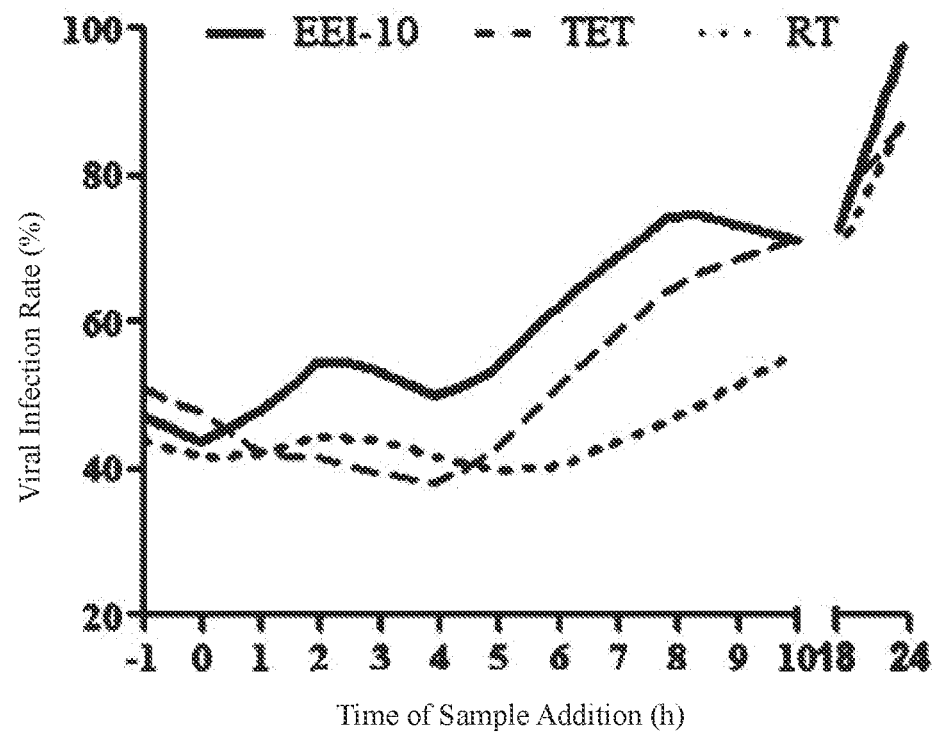
FIG. 5 shows that a drug TOA (Time of addition) experiment in embodiment 4 indicates that berbamine dihydrochloride acts on the entering stage of the virus; and in FIG. 5, TET represents a treatment with tetrandrine, EEI-10 represents a treatment with berbamine dihydrochloride, and RT represents a treatment with efavirenz.

The action link of the drug could be preliminarily judged by determining the failure time of the drug when a single infection of EBOV was conducted. As shown in FIG. 5, berbamine dihydrochloride showed a very strong inhibition effect at the early stage of viral entry, and had no inhibition effect on virus infection after the virus completed the adsorption process. This was consistent with the action time of the EBOV entry inhibitor tetrandrine. Non-nucleoside reverse transcriptase inhibitor efavirenz still had an inhibition effect on the virus at 6 h. These results indicated that berbamine dihydrochloride played a role after the virus bound to the host and before membrane fusion between the virus and the host occurred.

Embodiment 5. Evaluation of Compounds Using Marburg Recombinant Virus and Lassa Recombinant Virus Models The Ebola virus belonged to the family of filoviridae. Based on a recombinant virus technology, two other recombinant filovirus strain models, respectively of a Marburg recombinant virus (the MARV-GP-expressing pseudovirus MARV-GP/HIV-luc) and a Lassa recombinant virus (the LASV-GP-expressing pseudovirus LASV-GP/HIV-luc), had been established. The preparation methods of the MARV-GP-expressing pseudovirus MARV-GP/HIV-luc and the LASV-GP-expressing pseudovirus LASV-GP/HIV-luc were both different from the preparation methods of the EBOV-Zaire GP/HIV-luc only in that the pZEBOV-GP in the preparation method of the EBOV-Zaire GP/HIV-luc was replaced by pMARV-GP and pLASV-GP respectively, with other operations being exactly the same.

PMARV-GP was a recombinant expression plasmid expressing the glycoprotein of the Marburg virus, which was obtained by inserting positions 5941-7986 of the glycoprotein GP gene of the Marburg virus (GenBank Accession No. NC_001608.3) (Update Date 12 Nov. 2014) into the vector pcDNA3.1(+).

PLASV-GP was a recombinant expression plasmid expressing the glycoprotein of the Lassa virus, which was obtained by inserting positions 1872-3347 of the glycoprotein GP gene of the Lassa virus (GenBank Accession No. J04324.1) (Update Date Jun. 23, 2010) into the vector pcDNA3.1(+).

Figure 6:
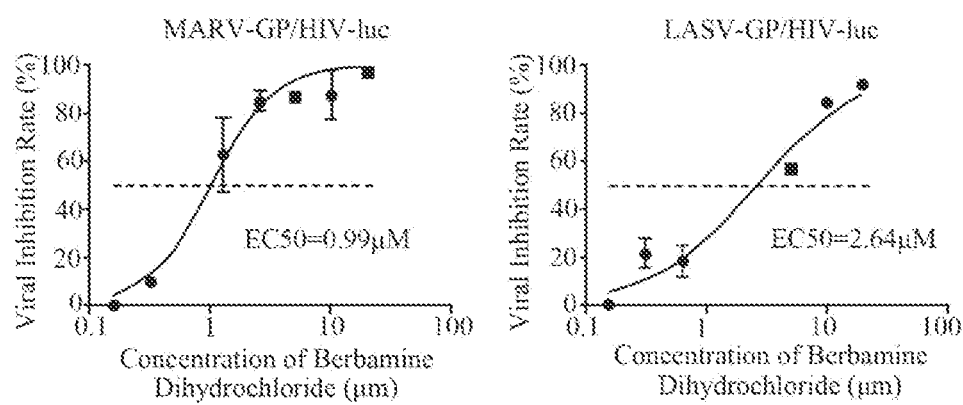
FIG. 6 shows that berbamine dihydrochloride has inhibition effect on both the MARV-GP/HIV-luc recombinant virus and the LASV-GP/HIV-luc recombinant virus in embodiment 5.

Referring to the method of Embodiment 3, the semi-maximum effect concentrations of berbamine dihydrochloride against the Marburg virus and the Lassa virus were determined using the recombinant virus models of MARV-GP/HIV-luc and LASV-GP/HIV-luc. As shown in FIG. 6, berbamine dihydrochloride could inhibit the Marburg virus and the Lassa virus from entering the host, with EC50s of 0.99 µM and 2.64 µM respectively. This study suggested that berbamine dihydrochloride had a broad-spectrum antiviral effect. It could be seen from the protein sequence alignment result that, the sequence homology in the GP protein between the two strains of Ebola virus and Marburg virus was only 23%. The application of multi-strain virus model to evaluate compounds would be beneficial to the discovery of broad-spectrum antiviral drugs, and would facilitate the study of a drug action mechanism.

Embodiment 6. Determination of the Capability of Berbamine Dihydrochloride of Binding to the Target Protein GPcl In Vitro by Using a BioLayer Interferometry Technology The envelope surface glycoprotein GP of the Ebola virus was subjected to enzyme digestion treatment by a host protease Cathepsin in an endosome, and thus converted into a primed glycoprotein GPcl, so as to expose a receptor binding site. In order to verify that berbamine dihydrochloride specifically inhibited viral entry by binding to the target protein GPcl, the capability of berbamine dihydrochloride of binding to the target protein GPcl was determined in vitro by using a BioLayer Interferometry (BLI) technology based on an optical fiber biosensor. The BLI technology could track the interactions between biomolecules in real time, and was an ideal choice for studying the interactions between proteins and other biomolecules. The specific steps were as follows.

Since a Super streptavidin (SSA) biosensor was used in the experiment, a biotinylation treatment of the target protein GPcl was required first. Biotin (EZ-Link™ NHS-LC-LC-Biotin, Cat. #21343, ThermoScientific™) was mixed with the purified target protein GPcl according to a molar ratio of 3:1, reacted at room temperature for 1 hour, and then passed through a desalting column (Zeba™ Spin Desalting Columns, Cat. #89883, Thermo) to remove unreacted biotin, and thus a biotinylated target protein GPcl was obtained.

Combined with the experiment, and by using an Octet RED96 (ForteBio, Inc., CA, USA) instrument, the experiment was mainly carried out by the following steps: 1) detecting a baseline: immersing a SSA sensor into a buffer solution and standing for 120 s to reach an equilibrium; 2) incubating the biotinylated target protein GPcl onto the sensor: moving a sensor probe into the biotinylated GPcl protein solution (50 μg/ml) and standing for 600 s to fix the protein on the SSA sensor; 3) blocking the sensor: moving the sensor into a solution containing 5 μM biocytin (EZ-Biocytin, Cat. #28022, Thermo) and blocking for 60 s; 4) detecting the baseline for the second time: moving the sensor into a buffer solution and standing for 120 s to reach an equilibrium; 5) binding: moving the sensor into the compound solution and standing for 60 s to measure a Kon value; and 6) dissociating: moving the sensor into the buffer solution and standing for 60 s to obtain a Koff value. The buffer solution used in the experiment was PBS (for dissolution of protein) and PBS+5% DMSO (for dissolution of berbamine dihydrochloride). In this experiment, the sample loading and detection were carried out separately. A first microplate contained 3 columns, where the first column was PBS as a baseline, the second column was the biotinylated target protein GPcl for sample loading, and the third column was 5 μM biocytin for blocking. After sample loading, the sensor detected a second microplate, where the first to sixth columns were PBS+5% DMSO, and the seventh to twelfth columns were berbamine dihydrochloride with a concentration gradient from low to high concentrations (31.25 μM-500 μM). In this process, 5 different concentrations of berbamine dihydrochloride solutions were used to obtain the final kinetic curves. The experimental data was analyzed by using a ForteBio data analysis software DataAnalysis 9.0. The dissociation rate constant KD=Koff/Kon.

Figure 7:
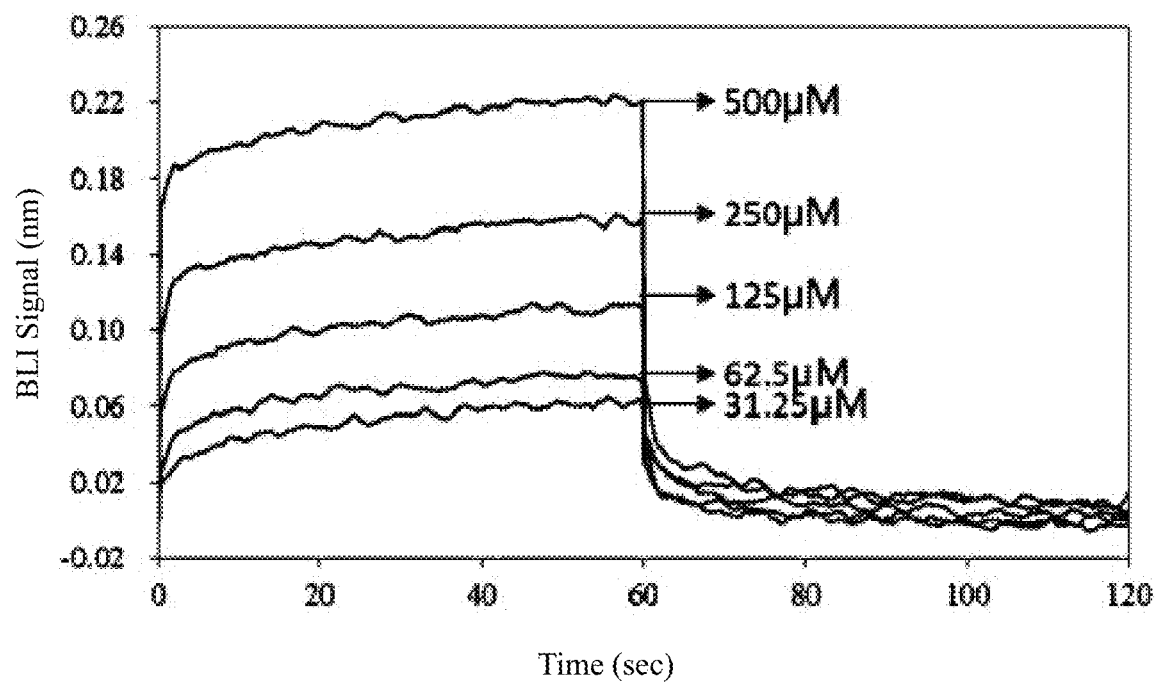
FIG. 7 shows a kinetic binding curve of different concentrations of berbamine dihydrochloride and the target protein GPcl as measured in vitro by a BioLayer Interferometry technology.

The horizontal ordinate in FIG. 7 was the reaction time in seconds. The vertical ordinate was the signal intensity in nm of the interaction between GPcl and berbamine dihydrochloride. The results showed that berbamine dihydrochloride could bind to the GPcl protein.

Although the anti-virus mechanism of the technical solution of the present invention is specifically illustrated by taking EBVO as an example in the present invention, the claimed scope of the present invention for use of berbamine dihydrochloride or a pharmaceutically acceptable salt thereof is not limited to EBOV. Any virus suitable for the above anti-virus mechanism is within the scope of the virus described in the present invention. For example, it can be other four subtypes of EBOV, and other viruses of filoviridae such as the Marburg virus, the Lassa virus (LASV), etc.

The present invention has been described in detail above. Although specific embodiments of the present invention have been given, it should be understood that the present invention can be further modified. In summary, according to the principle of the present invention, this application is intended to encompass any change to, use of, or modification to the present invention, including changes, which have departed from the scope disclosed in this application, as made by using conventional techniques known in the art. Application of some basic features can be done in accordance with the scope of the following appended claims.

What is claimed is:

1. A method for treating and/or preventing a viral hemorrhagic fever, comprising administrating a product to a subject in need, wherein the product comprises berbamine dihydrochloride or a pharmaceutically acceptable salt thereof and appropriate carrier or excipient; wherein the viral hemorrhagic fever is a disease caused by a virus capable of binding to berbamine dihydrochloride or a pharmaceutically acceptable salt thereof through a primed glycoprotein.

2. The method of claim 1, wherein the viral hemorrhagic fever is an Ebola hemorrhagic fever, a Marburg hemorrhagic fever and/or a Lassa fever.

3. The method of claim 1, wherein the product is in dosage form of a common preparation, a sustained-release preparation, a controlled-release preparation, or a microparticle administration system.

4. The method of claim 1, wherein the product is administered by injection, cavitary mucosal drug delivery, pulmonary administration, or mucosal administration.

* * * * *